(12) United States Patent
Bellisario et al.

(10) Patent No.: US 9,155,862 B2
(45) Date of Patent: Oct. 13, 2015

(54) SYMMETRICAL TIP ACUTE CATHETER

(71) Applicant: Covidien LP, Mansfield, MA (US)

(72) Inventors: Marc Bellisario, Tewksbury, MA (US); David Thomashey, E. Walpole, MA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/629,915

(22) Filed: Sep. 28, 2012

(65) Prior Publication Data

US 2014/0094741 A1    Apr. 3, 2014

(51) Int. Cl.
*A61M 1/00*    (2006.01)
*A61M 25/00*    (2006.01)

(52) U.S. Cl.
CPC ......... *A61M 25/0071* (2013.01); *A61M 25/003* (2013.01); *A61M 25/007* (2013.01); *A61M 25/0069* (2013.01); *A61M 2025/0031* (2013.01); *A61M 2025/0073* (2013.01)

(58) Field of Classification Search
CPC .......... A61M 25/007; A61M 25/0068; A61M 2025/0037; A61M 2025/0031
USPC ..................... 604/29, 43, 264, 523
See application file for complete search history.

(56) References Cited

U.S. PATENT DOCUMENTS

| | | | |
|---|---|---|---|
| 701,075 | A | 5/1902 | McCully |
| 2,541,691 | A | 2/1951 | Eicher |
| D208,838 | S | 10/1967 | St. Amand |
| 4,134,402 | A | 1/1979 | Mahurkar |
| D254,270 | S | 2/1980 | Ziegler |
| 4,403,983 | A | 9/1983 | Edelman et al. |
| D272,651 | S | 2/1984 | Mahurkar |
| 4,493,696 | A | 1/1985 | Uldall |
| 4,568,329 | A * | 2/1986 | Mahurkar ........... 604/43 |
| 4,583,968 | A | 4/1986 | Mahurkar |
| 4,601,697 | A | 7/1986 | Mammolenti et al. |
| 4,619,643 | A | 10/1986 | Bai |

(Continued)

FOREIGN PATENT DOCUMENTS

| | | |
|---|---|---|
| CA | 2 389 277 | 10/2001 |
| EP | 0 107 810 | 5/1984 |

(Continued)

OTHER PUBLICATIONS

First Office Action issued in Chinese Appl. No. 201210059962.5 dated Apr. 26, 2013.

(Continued)

*Primary Examiner* — Gerald Landry, II
(74) *Attorney, Agent, or Firm* — John Paul Mello, Esq.

(57) ABSTRACT

A medical catheter assembly includes a catheter tip coupled to a distal end of an elongate catheter member and is symmetric about a plane defined by a septum of the elongate catheter member. The catheter tip defines first and second lumens, and the catheter tip defines first and second openings in the distal portion of the catheter tip. Each opening of the catheter tip is defined by a respective side surface of the catheter tip. Each opening is in fluid communication with a respective one of the first and second lumens of the catheter tip and with a respective one of a pair of lumens defined by the elongate catheter member. The distance between upper and lower surfaces of the catheter tip decreases from a distal end of the proximal portion toward a closed distal end of the catheter tip.

9 Claims, 13 Drawing Sheets

(56) References Cited

U.S. PATENT DOCUMENTS

| | | | |
|---|---|---|---|
| 4,626,240 | A | 12/1986 | Edelman et al. |
| 4,643,711 | A | 2/1987 | Bates |
| D289,682 | S | 5/1987 | Dragan |
| 4,675,004 | A | 6/1987 | Hadford et al. |
| 4,682,978 | A | 7/1987 | Martin |
| 4,687,471 | A | 8/1987 | Twardowski et al. |
| 4,692,141 | A | 9/1987 | Mahurkar |
| 4,769,005 | A | 9/1988 | Ginsburg et al. |
| 4,770,652 | A | 9/1988 | Mahurkar |
| 4,772,268 | A | 9/1988 | Bates |
| 4,772,269 | A | 9/1988 | Twardowski et al. |
| 4,795,439 | A | 1/1989 | Guest |
| 4,808,155 | A | 2/1989 | Mahurkar |
| 4,808,156 | A | 2/1989 | Dean |
| 4,842,582 | A | 6/1989 | Mahurkar |
| 4,894,057 | A | 1/1990 | Howes |
| 4,895,561 | A | 1/1990 | Mahurkar |
| 4,897,079 | A | 1/1990 | Zaleski et al. |
| 4,904,238 | A | 2/1990 | Williams |
| 4,961,809 | A | 10/1990 | Martin |
| 4,995,865 | A * | 2/1991 | Gahara et al. .................. 604/43 |
| 5,009,636 | A | 4/1991 | Wortley et al. |
| 5,041,083 | A | 8/1991 | Tsuchida et al. |
| 5,053,004 | A | 10/1991 | Markel et al. |
| 5,053,023 | A | 10/1991 | Martin |
| 5,057,073 | A | 10/1991 | Martin |
| 5,059,170 | A | 10/1991 | Cameron |
| 5,085,632 | A | 2/1992 | Ikada et al. |
| 5,106,368 | A | 4/1992 | Uldall et al. |
| 5,135,599 | A | 8/1992 | Martin et al. |
| 5,156,592 | A | 10/1992 | Martin et al. |
| 5,159,050 | A | 10/1992 | Onwumere |
| 5,167,623 | A | 12/1992 | Cianci et al. |
| 5,171,227 | A | 12/1992 | Twardowski et al. |
| 5,188,593 | A | 2/1993 | Martin |
| 5,190,520 | A | 3/1993 | Fenton, Jr. et al. |
| 5,195,962 | A | 3/1993 | Martin et al. |
| 5,197,951 | A | 3/1993 | Mahurkar |
| 5,209,723 | A | 5/1993 | Twardowski et al. |
| 5,219,335 | A | 6/1993 | Willard et al. |
| 5,221,255 | A | 6/1993 | Mahurkar et al. |
| 5,221,256 | A | 6/1993 | Mahurkar |
| 5,273,527 | A | 12/1993 | Schatz et al. |
| 5,308,338 | A | 5/1994 | Helfrich |
| 5,318,518 | A | 6/1994 | Plechinger et al. |
| 5,342,383 | A | 8/1994 | Thomas |
| 5,346,471 | A | 9/1994 | Raulerson |
| 5,348,536 | A * | 9/1994 | Young et al. .................. 604/43 |
| 5,360,397 | A | 11/1994 | Pinchuk |
| 5,364,344 | A | 11/1994 | Beattie et al. |
| 5,374,245 | A * | 12/1994 | Mahurkar .................. 604/43 |
| 5,378,230 | A | 1/1995 | Mahurkar |
| 5,380,276 | A | 1/1995 | Miller et al. |
| 5,395,316 | A | 3/1995 | Martin |
| 5,403,291 | A | 4/1995 | Abrahamson |
| 5,405,341 | A | 4/1995 | Martin |
| 5,419,777 | A | 5/1995 | Hofling |
| 5,451,206 | A | 9/1995 | Young |
| 5,464,398 | A | 11/1995 | Haindl |
| 5,472,417 | A | 12/1995 | Martin et al. |
| 5,480,380 | A | 1/1996 | Martin |
| 5,486,159 | A | 1/1996 | Mahurkar |
| 5,489,278 | A | 2/1996 | Abrahamson |
| 5,509,897 | A | 4/1996 | Twardowski et al. |
| 5,549,541 | A | 8/1996 | Muller |
| 5,554,136 | A | 9/1996 | Luther |
| 5,556,390 | A | 9/1996 | Hicks |
| 5,562,640 | A | 10/1996 | McCabe et al. |
| 5,569,182 | A | 10/1996 | Twardowski et al. |
| 5,571,093 | A | 11/1996 | Cruz et al. |
| 5,607,440 | A | 3/1997 | Danks et al. |
| D381,420 | S | 7/1997 | Musgrave et al. |
| D384,411 | S | 9/1997 | Musgrave et al. |
| D384,741 | S | 10/1997 | Musgrave et al. |
| 5,683,640 | A | 11/1997 | Miller et al. |
| 5,685,867 | A | 11/1997 | Twardowski et al. |
| 5,702,365 | A | 12/1997 | King |
| 5,707,351 | A | 1/1998 | Dorsey, III |
| 5,718,678 | A | 2/1998 | Fleming, III |
| 5,725,495 | A | 3/1998 | Strukel et al. |
| 5,776,092 | A | 7/1998 | Farin et al. |
| 5,776,096 | A | 7/1998 | Fields |
| 5,782,797 | A | 7/1998 | Schweich, Jr. et al. |
| 5,785,678 | A | 7/1998 | Griep et al. |
| 5,788,680 | A | 8/1998 | Linder |
| 5,788,681 | A | 8/1998 | Weaver et al. |
| 5,797,869 | A | 8/1998 | Martin et al. |
| 5,807,311 | A | 9/1998 | Palestrant |
| 5,807,329 | A | 9/1998 | Gelman |
| 5,810,789 | A | 9/1998 | Powers et al. |
| 5,830,184 | A | 11/1998 | Basta |
| 5,830,196 | A * | 11/1998 | Hicks .................. 604/523 |
| 5,858,009 | A | 1/1999 | Jonkman |
| 5,868,717 | A | 2/1999 | Prosl |
| 5,947,940 | A | 9/1999 | Beisel |
| 5,947,953 | A | 9/1999 | Ash et al. |
| 5,961,485 | A | 10/1999 | Martin |
| 5,961,486 | A | 10/1999 | Twardowski et al. |
| 5,976,103 | A | 11/1999 | Martin |
| 5,989,206 | A | 11/1999 | Prosl et al. |
| 5,989,213 | A | 11/1999 | Maginot |
| 5,993,437 | A | 11/1999 | Raoz |
| 6,001,079 | A | 12/1999 | Pourchez |
| 6,004,310 | A | 12/1999 | Bardsley et al. |
| 6,063,099 | A | 5/2000 | Danks et al. |
| 6,086,565 | A | 7/2000 | Ouchi |
| 6,099,519 | A | 8/2000 | Olsen et al. |
| 6,123,725 | A | 9/2000 | Aboul-Hosn |
| 6,126,631 | A | 10/2000 | Loggie |
| 6,143,893 | A | 11/2000 | Tanzi et al. |
| 6,146,354 | A | 11/2000 | Beil |
| 6,152,910 | A | 11/2000 | Agro et al. |
| 6,152,912 | A | 11/2000 | Jansen et al. |
| 6,156,016 | A | 12/2000 | Maginot |
| 6,190,349 | B1 | 2/2001 | Ash et al. |
| 6,190,357 | B1 | 2/2001 | Ferrari et al. |
| 6,190,371 | B1 | 2/2001 | Maginot et al. |
| 6,200,338 | B1 | 3/2001 | Solomon et al. |
| 6,206,849 | B1 | 3/2001 | Martin et al. |
| 6,273,875 | B1 | 8/2001 | Siman et al. |
| 6,280,423 | B1 | 8/2001 | Davey et al. |
| 6,283,951 | B1 | 9/2001 | Flaherty et al. |
| 6,293,927 | B1 | 9/2001 | McGuckin, Jr. |
| 6,299,444 | B1 | 10/2001 | Cohen |
| 6,325,790 | B1 * | 12/2001 | Trotta .................. 604/523 |
| 6,342,120 | B1 | 1/2002 | Basta |
| 6,346,090 | B1 | 2/2002 | Liska et al. |
| 6,394,141 | B2 | 5/2002 | Wages et al. |
| 6,409,700 | B1 | 6/2002 | Siegel, Jr. et al. |
| 6,423,050 | B1 | 7/2002 | Twardowski |
| 6,428,502 | B1 | 8/2002 | Lang |
| 6,447,488 | B2 | 9/2002 | Estabrook et al. |
| 6,461,321 | B1 | 10/2002 | Quinn |
| 6,475,207 | B1 | 11/2002 | Maginot et al. |
| 6,482,169 | B1 | 11/2002 | Kuhle |
| 6,506,182 | B2 | 1/2003 | Estabrook et al. |
| 6,533,750 | B2 | 3/2003 | Sutton et al. |
| 6,579,261 | B1 | 6/2003 | Kawamura |
| 6,585,705 | B1 | 7/2003 | Maginot et al. |
| 6,592,542 | B2 | 7/2003 | Childers et al. |
| 6,592,565 | B2 | 7/2003 | Twardowski |
| 6,595,966 | B2 | 7/2003 | Davey et al. |
| 6,620,118 | B1 | 9/2003 | Prosl et al. |
| 6,623,448 | B2 * | 9/2003 | Slater .................. 604/95.01 |
| 6,638,242 | B2 | 10/2003 | Wilson et al. |
| 6,692,473 | B2 | 2/2004 | St. Cyr et al. |
| 6,695,832 | B2 | 2/2004 | Schon et al. |
| 6,719,749 | B1 | 4/2004 | Schweikert et al. |
| 6,723,084 | B1 | 4/2004 | Maginot et al. |
| 6,730,096 | B2 | 5/2004 | Basta |
| 6,743,218 | B2 | 6/2004 | Maginot et al. |
| 6,749,580 | B2 | 6/2004 | Work et al. |
| 6,758,836 | B2 | 7/2004 | Zawacki |
| 6,786,884 | B1 | 9/2004 | DeCant, Jr. et al. |

(56) References Cited

U.S. PATENT DOCUMENTS

| | | |
|---|---|---|
| 6,808,510 B1 | 10/2004 | DiFiore |
| 6,814,718 B2 | 11/2004 | McGuckin, Jr. et al. |
| 6,858,019 B2 | 2/2005 | McGuckin, Jr. et al. |
| 6,872,198 B1 | 3/2005 | Wilson et al. |
| 6,911,014 B2 | 6/2005 | Wentling et al. |
| 6,921,396 B1 | 7/2005 | Wilson et al. |
| 6,942,635 B2 | 9/2005 | Rosenblatt et al. |
| 6,942,653 B2 | 9/2005 | Quinn |
| 6,966,886 B2 | 11/2005 | Appling |
| 6,969,381 B2 | 11/2005 | Voorhees |
| 6,976,973 B1 | 12/2005 | Ruddell et al. |
| 6,986,752 B2 | 1/2006 | McGuckin, Jr. et al. |
| 6,991,625 B1 | 1/2006 | Gately et al. |
| 7,008,395 B1 | 3/2006 | Loggie |
| 7,008,412 B2 | 3/2006 | Maginot |
| 7,011,645 B2 | 3/2006 | McGuckin, Jr. et al. |
| 7,013,928 B2 | 3/2006 | Navis |
| 7,029,467 B2 * | 4/2006 | Currier et al. ................. 604/525 |
| 7,048,680 B2 | 5/2006 | Viole et al. |
| 7,066,914 B2 | 6/2006 | Andersen |
| 7,077,829 B2 | 7/2006 | McGuckin, Jr. et al. |
| 7,090,654 B2 | 8/2006 | Lotito et al. |
| 7,141,035 B2 | 11/2006 | Haggstrom |
| 7,322,953 B2 | 1/2008 | Redinger |
| 7,569,029 B2 | 8/2009 | Clark |
| 7,776,005 B2 | 8/2010 | Haggstrom et al. |
| 8,092,415 B2 | 1/2012 | Moehle et al. |
| 8,292,841 B2 * | 10/2012 | Gregersen ....................... 604/29 |
| 2002/0121282 A1 | 9/2002 | McGuckin |
| 2002/0156430 A1 | 10/2002 | Haarala et al. |
| 2002/0165492 A1 | 11/2002 | Davey et al. |
| 2003/0032918 A1 | 2/2003 | Quinn |
| 2003/0093029 A1 | 5/2003 | McGuckin, Jr. et al. |
| 2003/0144623 A1 * | 7/2003 | Heath et al. .................. 604/4.01 |
| 2003/0191425 A1 | 10/2003 | Rosenblatt |
| 2004/0006318 A1 | 1/2004 | Periakaruppan et al. |
| 2004/0167463 A1 | 8/2004 | Zawacki et al. |
| 2004/0249337 A1 | 12/2004 | DiFiore |
| 2005/0033222 A1 | 2/2005 | Haggstrom et al. |
| 2005/0085765 A1 | 4/2005 | Voorhees |
| 2005/0090776 A1 | 4/2005 | McGuckin, Jr. et al. |
| 2005/0182352 A1 * | 8/2005 | DiMatteo et al. ............... 604/43 |
| 2005/0215978 A1 | 9/2005 | Ash |
| 2005/0228339 A1 | 10/2005 | Clark |
| 2005/0267400 A1 | 12/2005 | Haarala et al. |
| 2005/0288623 A1 | 12/2005 | Hjalmarsson |
| 2006/0004325 A1 | 1/2006 | Hamatake et al. |
| 2007/0100298 A1 | 5/2007 | Appling |
| 2008/0082080 A1 | 4/2008 | Braga |
| 2009/0118661 A1 * | 5/2009 | Moehle et al. ............... 604/6.16 |
| 2009/0192435 A1 * | 7/2009 | Gregersen .................... 604/6.16 |
| 2009/0318991 A1 * | 12/2009 | Tomaschko et al. ............ 607/10 |
| 2010/0063480 A1 * | 3/2010 | Shireman ...................... 604/528 |
| 2011/0077577 A1 | 3/2011 | Sansoucy |
| 2012/0089115 A1 * | 4/2012 | Difiore et al. ................. 604/503 |

FOREIGN PATENT DOCUMENTS

| | | |
|---|---|---|
| EP | 0 299 622 | 1/1989 |
| EP | 0 341 721 | 11/1989 |
| EP | 0 554 722 | 8/1993 |
| EP | 0 623 356 | 11/1994 |
| EP | 0 322 225 | 2/1995 |
| EP | 0 555 780 | 9/1999 |
| EP | 1 905 476 | 4/2008 |
| EP | 2119468 A1 | 11/2009 |
| FR | 2 326 941 | 10/1976 |
| GB | 2028136 | 3/1980 |
| JP | 08103492 | 4/1996 |
| JP | 8308933 | 11/1996 |
| JP | H11512625 A | 11/1999 |
| JP | 2004174130 A | 6/2004 |
| JP | 2006095134 A | 4/2006 |
| JP | 2007502164 A | 2/2007 |
| JP | 2007521913 A | 8/2007 |
| JP | 2008503274 A | 2/2008 |
| JP | 2011502583 A | 1/2011 |
| JP | 2012520092 A | 9/2012 |
| WO | WO 92/13584 | 8/1992 |
| WO | WO 92-14500 | 9/1992 |
| WO | WO 95-04567 | 2/1995 |
| WO | WO 95-10317 | 4/1995 |
| WO | WO 97-37699 | 10/1997 |
| WO | 9748425 A2 | 12/1997 |
| WO | WO 98-41277 | 9/1998 |
| WO | WO 99-38550 | 8/1999 |
| WO | WO 99-65557 | 12/1999 |
| WO | WO 01-91845 | 12/2001 |
| WO | WO 02-13899 | 2/2002 |
| WO | WO 02-18004 | 3/2002 |
| WO | WO 03-033049 | 4/2003 |
| WO | WO 03-066148 | 8/2003 |
| WO | WO 2004-093956 | 11/2004 |
| WO | WO 2005-023336 | 3/2005 |
| WO | WO 2005-077449 | 8/2005 |
| WO | WO 2005-084741 | 9/2005 |
| WO | WO 2006-014339 | 2/2006 |
| WO | 2007/111874 A2 | 10/2007 |
| WO | WO 2008-155145 A1 | 12/2008 |

OTHER PUBLICATIONS

Kaneko, Takashi, Seikei-Kakou (Molding Process), pp. 404-407, vol. 15, No. 6 (2003) (Abstract Only).

Ishikawa, Kenji, Gosei-Jushi (Synthetic Resin), pp. 29-32, vol. 44, No. 4 (1998) (Abstract Only).

Office Action issued in corresponding Chinese Patent Application No. 200580041146.X dated Jun. 5, 2009.

European Search Report EP 10 18 4012 dated Oct. 28, 2011.

Bard Access Systems Power-Trialysis Short-Term Dialysis Catheter—Short-Term Triple Lumen Dialysis Catheter, Enhanced Acute Dialysis Care.

European Search Report from Application No. EP 13184881.4 dated Jan. 27, 2014.

Patent Examination Report No. 1 from counterpart Australian Patent Application No. 2013231077, dated Oct. 10, 2014, 3 pp.

Examiner's Report from counterpart Canadian Patent Application No. 2827630, dated Oct. 15, 2014, 2 pp.

Notice of Reasons for Rejection, and translation thereof, from counterpart Japanese Patent Application No. 2013199657, dated Sep. 4, 2014, 10 pp.

Notice of Reasons for Rejection, and translation thereof, from counterpart Japanese Patent Application No. 2013-199657, mailed May 7, 2015, 8 pp.

Notification of the First Office Action mailed Feb. 25, 2015, and translation thereof, from counterpart Chinese Application No. 201310596216.4, 17 pgs.

* cited by examiner

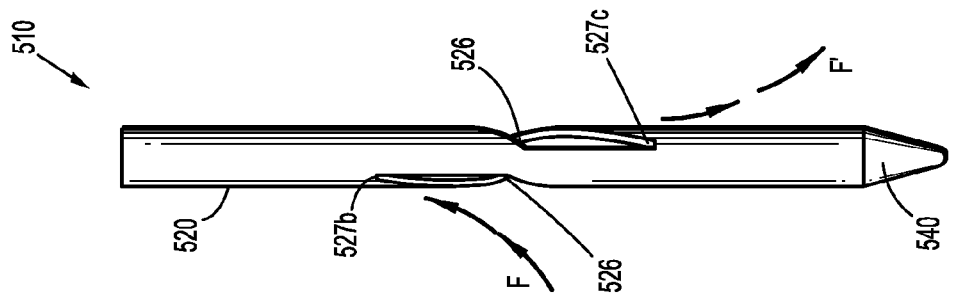
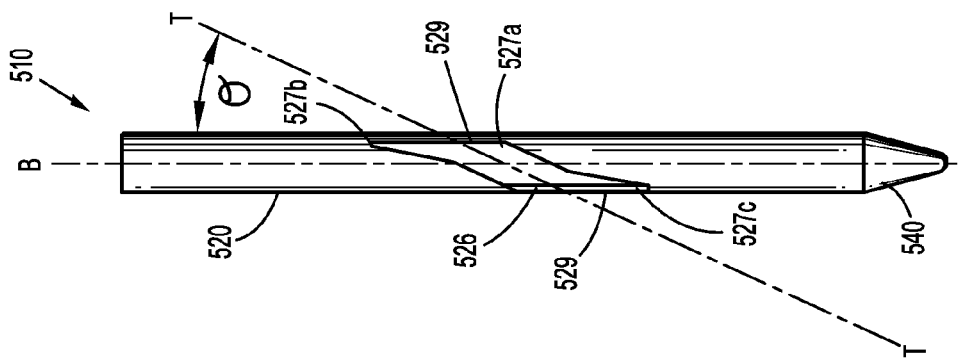
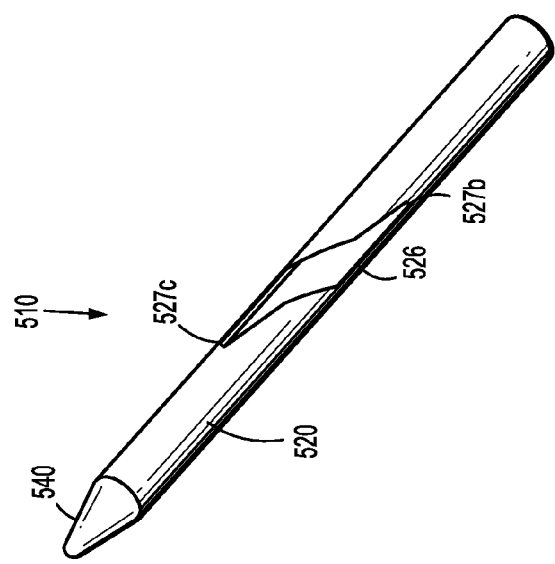

SYMMETRICAL TIP ACUTE CATHETER

TECHNICAL FIELD

The present disclosure relates to a catheter assembly, and, in particular, to a symmetrical tip acute catheter.

BACKGROUND

Catheters are flexible medical instruments intended for the withdrawal and introduction of fluids to and from body cavities, ducts and vessels. Catheters have particular application in hemodialysis procedures, in which blood is withdrawn from a blood vessel for treatment and subsequently returned to the blood vessel for circulation. Hemodialysis catheters can include multiple lumens, such as dual lumen or triple lumen catheters, which pemit bi-directional fluid flow within the catheter whereby one lumen, the arterial lumen, is dedicated for withdrawal of blood from a vessel and the other lumen, the venous lumen, is dedicated for returning purified blood to the vessel. During some hemodialysis procedures, a multiple lumen catheter is inserted into a body, and blood is withdrawn through the arterial lumen of the catheter. The withdrawn blood is directed to a hemodialysis unit which dialyzes, or purifies, the blood to remove waste and toxins Thereafter, the dialyzed blood is returned to the patient through the venous lumen of the catheter.

Generally, hemodialysis catheters are categorized as either chronic or acute in nature. Chronic catheters typically remain in place for extended periods of time, and may be implanted via surgical dissection. Acute catheters, by comparison, are designed to be placed in a patient under emergent circumstances in which speed of placement is desirable. Acute catheters typically remain in place for only a few days. As such, acute catheters are often more rigid than chronic catheters, given the urgency of placement.

In hemodialysis catheters, recirculation can occur when purified blood exiting the venous lumen of the catheter is withdrawn directly into the arterial lumen such that purified blood is returned to the dialyzer. As such, recirculation increases the time required to complete the hemodialysis procedure.

SUMMARY

The present disclosure is directed to further improvements in hemodialysis catheters and systems used therewith. A catheter assembly includes an elongate catheter member, and a catheter tip. The elongate catheter member includes a septum defining at least a portion of each of a pair of internal lumens. The catheter tip is coupled to a distal end of the elongate catheter member and is symmetric about a plane defined by the septum. The catheter tip includes a distal portion and a proximal portion, an upper surface, a lower surface, and side surfaces between the upper and lower surfaces, the distal portion including a closed distal end. The catheter tip defines first and second lumens and first and second openings in the distal portion of the catheter tip. Each opening is defined by a respective side surface of the catheter tip. Each opening is in fluid communication with a respective one of the first and second lumens of the catheter tip and with a respective one of the first and second lumens of the elongate catheter member. The distance between the upper and lower surfaces of the catheter tip decreases from a distal end of the proximal end portion toward the closed distal end. The first and second openings are diametrically opposed to one another and may be laser-cut or otherwise formed to have contoured edges to reduce the likelihood of thrombus formation.

The first and second passages of the catheter tip are in fluid communication with a respective one of the pair of internal lumens of the elongate catheter member such that fluids may pass between the elongate catheter member, the catheter tip, and the first and second opening so that the catheter member is in fluid communication with an outside environment such as an internal body cavity. The pair of internal lumens may be configured for opposing bi-directional fluid flow, as in the case of hemodialysis procedures. In embodiments, one or more connecting members may be disposed between the elongate catheter member and the catheter tip, and the one or more connecting members may define channels to facilitate communication between the elongate catheter member and the catheter tip. Distal ends of the connecting members may be disposed adjacent the proximal ends of the first and second side openings such that fluids exit the connecting members upon reaching the proximal ends of the first and second side openings.

In embodiments, the distance between the upper and lower surfaces along the proximal portion increases in the distal direction adjacent the distal portion. In another embodiment, the proximal portion of the catheter tip is defined by a curved spheroid region. In still another embodiment, the first and second openings are each an elongate oval.

In a further embodiment of the present disclosure, the elongate catheter member defines a longitudinal axis and the first and second side openings are spaced a distance along the longitudinal axis from the distal end of the catheter tip. In another embodiment of the present disclosure, the first and second internal lumens are semicircular in cross-sectional shape.

In still another embodiment, the elongate catheter member and the catheter tip are coupled by at least one connecting member extending therebetween. The at least one connecting member defines a channel in fluid communication with the elongate catheter member and the catheter tip. The at least one connecting member may include a proximal end and a distal end, and the distal end of the connecting member is adjacent one of the first and second side openings. The first and second side openings each have a contoured perimeter.

In a further embodiment of the present disclosure, a medical catheter includes an elongate tubular member defining a pair of lumens and a longitudinal axis. A pair of diametrically opposed side openings in fluid communication with the respective pair of lumens. Each side opening has a proximal end and a distal end, and each side opening has an elongated substantially z-shaped configuration including a rectangular central portion defining a transverse axis and triangular proximally and distally extending portions. The triangular proximally extending portion defines an apex at the proximal end of the side opening and the triangular distally extending portion defines an apex at the distal end of the side opening. The transverse axis of the rectangular central portion defines an acute angle with the longitudinal axis of the elongate tubular member. The acute angle can be between about fifteen and about seventy-five degrees. In some embodiments, the elongate tubular member includes a septum defining at least a portion of each of the pair of lumens. The septum extends parallel to the longitudinal axis, and the elongate tubular member is symmetrical about a plane defined by the septum. In certain embodiments, the pair of side openings each have contoured edges. In some embodiments, the proximal and distal ends of each of the side openings are rounded.

Other aspects, features, and advantages will be apparent from the description and drawings, and from the claims.

BRIEF DESCRIPTION OF THE DRAWINGS

FIG. 8A is a perspective view of a catheter assembly including an elongate catheter member having a pair axially opposed and offset tapered slots.

FIG. 8B is a side view of the catheter assembly of FIG. 8A.

FIG. 8C is a top view of the catheter assembly of FIG. 8A.

DETAILED DESCRIPTION OF THE EMBODIMENTS

Embodiments of the presently disclosed catheters are discussed in terms of medical catheters for the administration of fluids and, more particularly, in terms of hemodialysis catheters. However, it is envisioned that the present disclosure may be employed with a range of catheter applications including surgical, diagnostic and related treatments of diseases and body ailments, of a subject. It is further envisioned that the principles relating to the presently disclosed catheters include, for example, hemodialysis, cardiac, abdominal, urinary, intestinal, in chronic and/or acute applications.

In the discussion that follows, the term "proximal" will refer to the portion of a structure closer to an operator, while the term "distal" or will refer to the portion further from the operator. As used herein, the term "subject" refers to a human patient or other animal. The term. "operator" refers to a doctor, nurse or other care provider and may include support personnel.

Figures 1, 2:
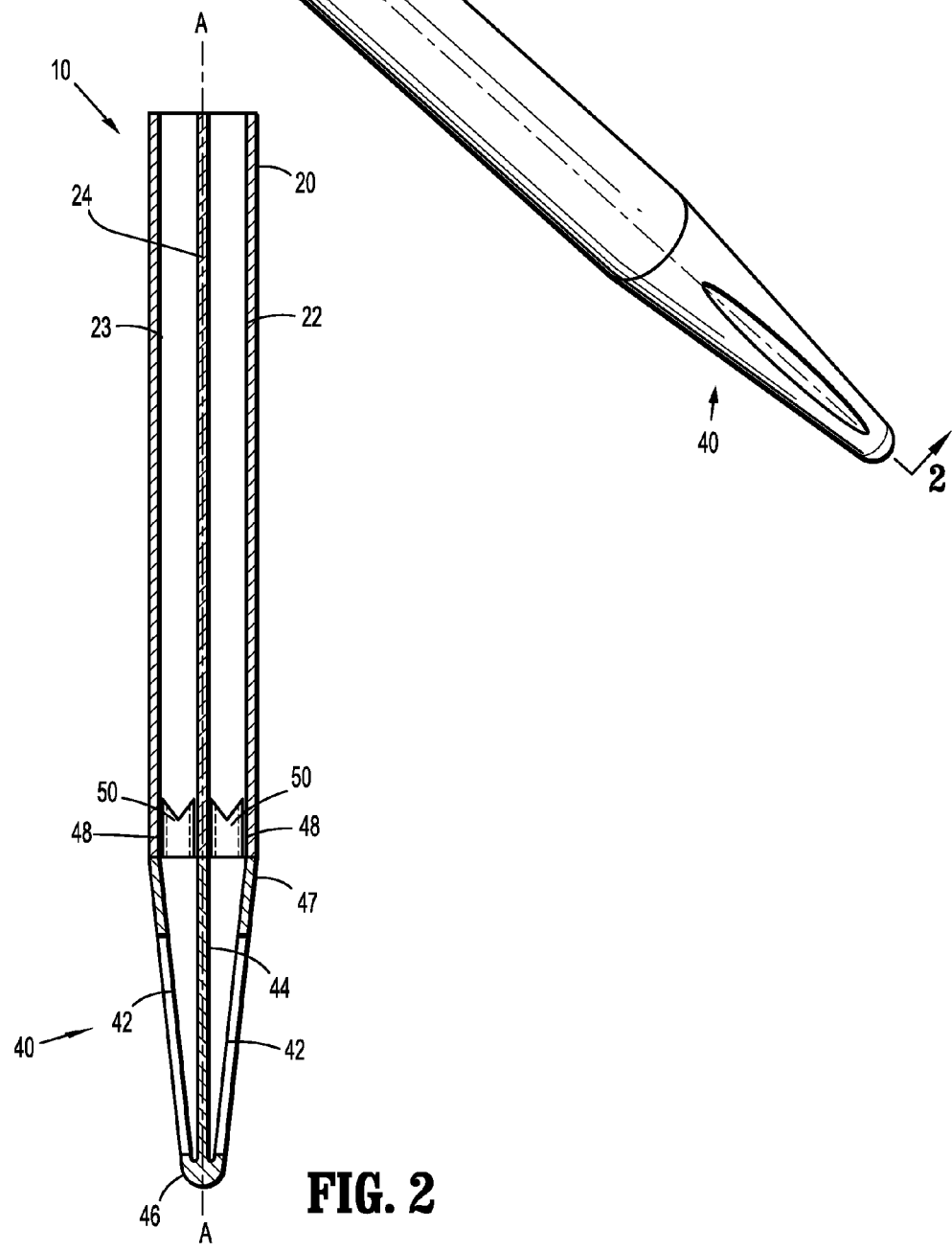
FIG. 1 is a perspective view of a distal portion of a medical catheter including an elongate catheter member and a tip.
FIG. 2 is a cross-sectional view of the medical catheter of FIG. 1, taken along section line 2-2 of FIG. 1.

Referring now to FIGS. 1-2, a catheter 1.0 includes a catheter body 20 and a catheter tip 40. The catheter body 20 defines a longitudinal axis "A" and may have a substantially circular cross-section. The catheter body 20 defines a pair of lumens 22, 23 extending the length of catheter 10. Alternately, the catheter 20 may define a third lumen for receiving a guidewire or the like. The lumens 22, 23 may include oblong, kidney-shaped, and/or D-shaped cross-sectional configurations. A septum 24 defined by the catheter body 20 is disposed between the adjacent lumens 22, 23 and can define at least a portion of each lumen 22, 23. In some embodiments, the catheter tip 40 has a substantially frusto-conical profile. The frusto-conical shape may aid in the insertion of the catheter 10, for example, in time-sensitive circumstances in which acute catheters are utilized.

The components of the catheter 10 may be fabricated from materials suitable for medical applications, such as, for example, polymers, silicone and/or polyurethane. The catheter body 20 is flexible and may be formed by injection molding or extrusion. The catheter body 20 may have a preformed bend in its normal condition to facilitate conforming to an internal body cavity or vessel in which the catheter body 20 is to be positioned. Alternatively, catheter body 20 may be substantially straight.

The catheter tip 40 may be fabricated from material suitable for medical application, including, for example, polymers, silicone, and/or polyurethane. In addition, the catheter tip 40 fabricated from the same material or a different material than catheter body 20. In some embodiments, catheter tip 40 is formed separately from catheter body 20 and is secured to a distal end portion of the catheter body 20. In certain embodiments, the catheter tip 40 is integrally or monolithically formed with the catheter body 20.

The catheter tip 40 includes a partition 44. The catheter tip 40 and the partition 44 define the lumens 42. An outer surface 47 of catheter tip 40 is tapered distally and approaches a closed, distal end 46 to aid insertion of the catheter 10. While the distal end 46 is shown as having a rounded, blunt profile, other shapes and profiles of the distal end 46 are possible. When the catheter body 20 and the catheter tip 40 are assembled, the lumens 42 of tip 40 are in fluid communication with and are aligned with the lumens 22, 23 of the catheter body 20. Similarly, the septum 24 and the partition 44 are aligned such that lumens 22, 23 and the respective lumens 42 define substantially parallel and separate pathways parallel to the longitudinal axis A along the catheter body 20. At least a distal portion of the septum 24 and a proximal portion of the partition 44 have substantially similar dimensions to provide a smooth transition between the catheter body 20 and the catheter tip 40.

The catheter tip 40 may include a pair of proximally extending connecting members 48 that are insertable into lumens 22, 23. The connecting members 48 are spaced to receive septum 24 and define channels 50. The channels 50 are in fluid communication with the lumens 22, 23 of the catheter body 20 when the catheter body 20 and the catheter tip 40 are assembled. The connecting members 48 may engage the lumens 22, 23 with an interference or frictional fit, forming a substantially fluid tight seal with lumens 22, 23. Alternatively or additionally, the connecting members 48 may be secured within with lumens 22, 23 using chemical adhesives or mechanical coupling, such as by welding.

Figure 3A:
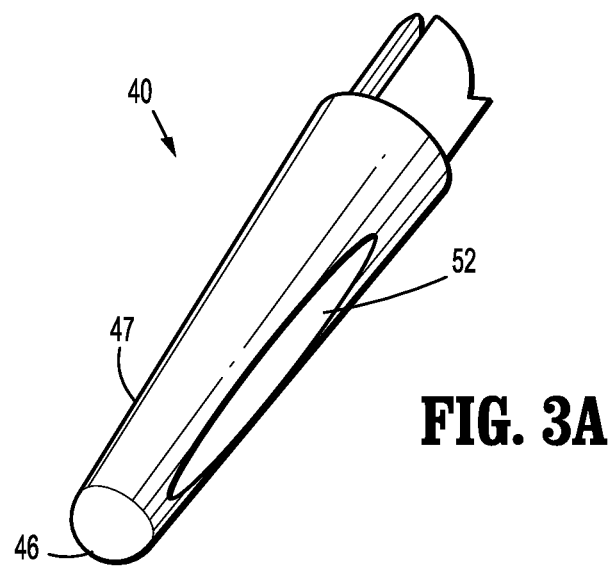
FIG. 3A is a perspective view of the tip of the catheter of FIG. 1 including a pair of side openings.
Figure 3B:
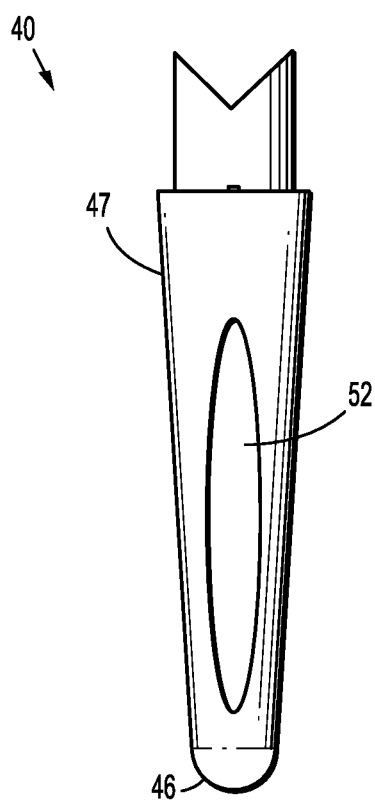
FIG. 3B is a side view of the catheter tip of FIG. 3A.
Figure 3C:
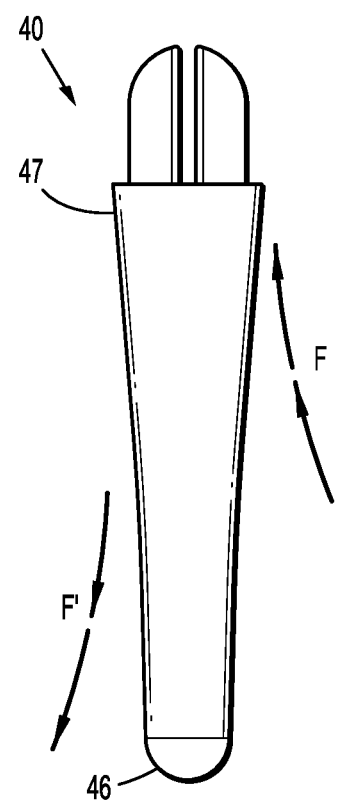
FIG. 3C is a top view of the catheter tip of FIG. 3A.

Referring now to FIGS. 3A-3C, a pair of side openings 52 is defined in the outer surface 47 of the catheter tip 40. The side openings 52 are substantially elongated, oval shaped slots that extend along catheter tip 40 and are symmetrical about the longitudinal axis A. The side openings 52 allow fluid streams F, F' to travel between an environment, such as an internal body cavity, and the internal lumens 42. The side openings 52 may have contoured edges formed, for example, by laser cutting, molding with catheter tip 40, and/or otherwise smoothed to minimize flow disruption and thrombus formation.

In a hemodialysis application, a proximal end portion of catheter body 20 (FIG. 1) is connected to a dialyzer (not shown) such that blood is withdrawn from a body vessel through one lumen 22 (FIG. 2), the arterial lumen, of the catheter body 20 via the respective side opening 52 of the catheter tip 40 and delivered to a dialyzer for purification. The purified blood is then returned to the body vessel through the second lumen 23, the venous lumen, of the catheter body 20 via the other side opening 52 of the catheter tip 40. Because of the symmetrical configuration of the catheter body 20, and the catheter tip 40 and the lumens 42, either lumen 22, 23 may serve as the arterial lumen or the venous lumen. Because of the configuration of the catheter tip 40, the blood flow stream F into the side opening 52 communicating with the arterial lumen 22 and the blood flow stream F' exiting the side opening 52 communicating with the venous lumen 23 are separated such that the degree of fluid recirculation is minimized.

The symmetrical nature of the catheter tip 40, the diametrically opposed positioning of side openings 52 along the tip 40, and the elongated shape of side openings 52 enables the spacing between the fluid stream F' exiting venous lumen 23 and the fluid stream F entering arterial lumen 22 to be maximized, which minimizes the degree of recirculation of purified blood between the venous lumen 23 and the arterial lumen 22 of the catheter 10 (FIG. 1). Specifically, blood enters proximally through the side openings 52 and exits distally through the side openings 52. The outer surface 47 and the distal end 46 of the catheter tip 40 provide spacing that substantially minimizes the fluid stream F' exiting the venous lumen 23 from migrating toward the fluid stream F entering the arterial lumen 22, which can also minimize the degree of fluid recirculation.

Figure 4A:
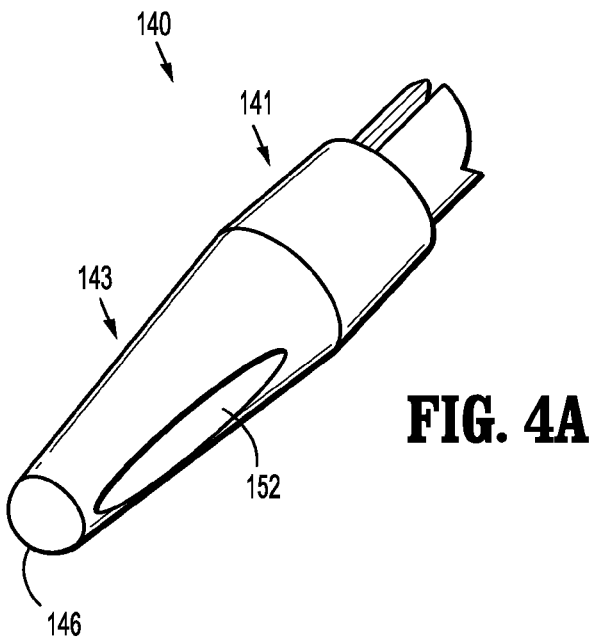
FIG. 4A is a perspective view of a catheter tip which includes a proximal portion having a changing diameter from the proximal portion to the distal portion.
Figure 4B:
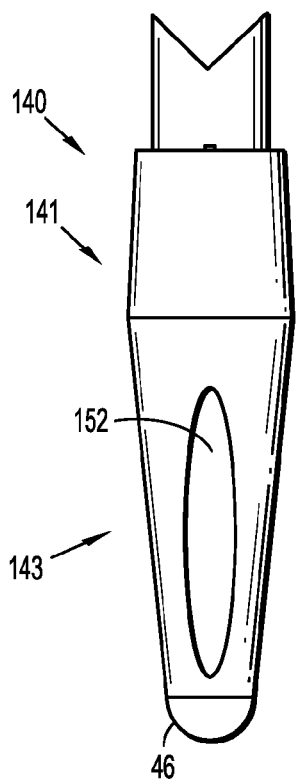
FIG. 4B is a side view of the catheter tip of FIG. 4A.
Figure 4C:
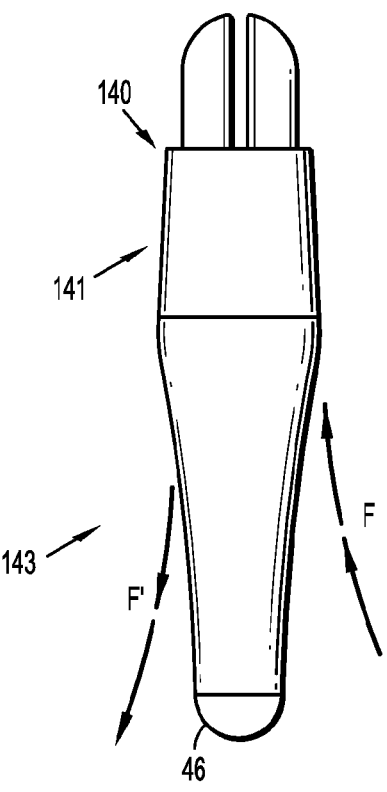
FIG. 4C is a top view of the catheter tip of FIG. 4A.

Referring now to FIGS. 4A-4C, a catheter tip 140 includes a proximal portion 141 and a distal portion 143. The distal portion 143 of the catheter tip 140 gradually tapers towards a closed distal end 146, which may have a blunt or atraumatic shape. The proximal portion 141 increases in diameter in a direction toward the distal portion 143. The increase in diameter along proximal portion 141 provides a radially expanding surface proximal to side openings 152. This radially expanding surface can direct fluid stream F' away from the side openings 152. The side openings 152 can be similar in configuration to side openings 52 and define an elongated oval configuration formed along the sides of the outer surface 147 of catheter tip 140. Because of the configuration of the catheter tip 140, the blood flow stream F into the side opening 152 communicating with an arterial lumen and the blood flow stream F' exiting the side opening 152 communicating with a venous lumen are separated such that the degree of fluid recirculation is minimized.

Figure 5A:
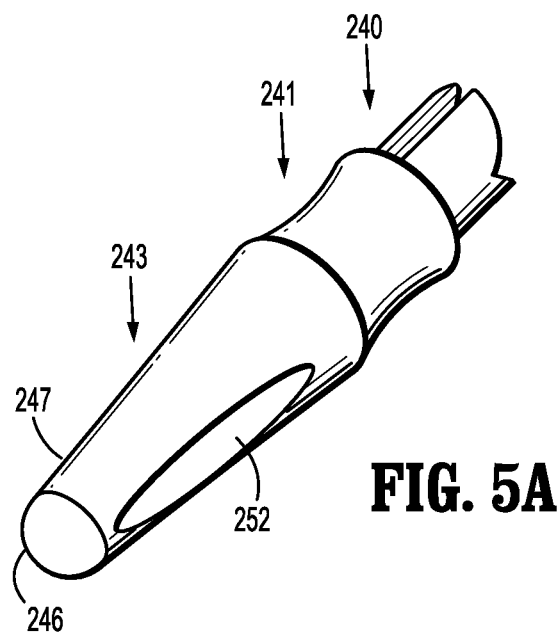
FIG. 5A is a perspective view of a catheter tip having a proximal portion with a curved spheroid region.
Figure 5B:
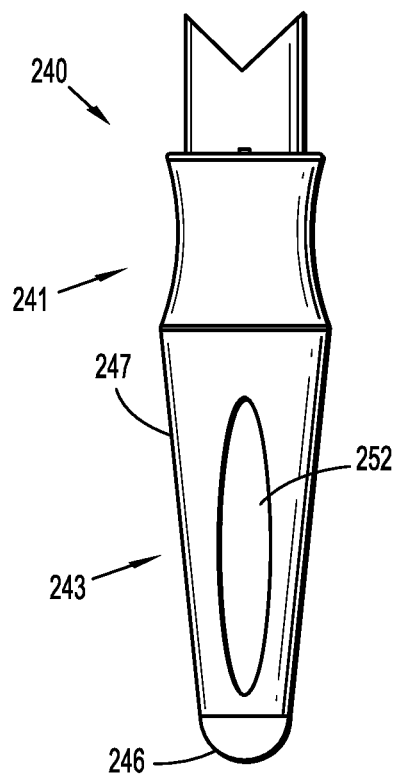
FIG. 5B is a side view of the catheter tip of FIG. 5A.
Figure 5C:
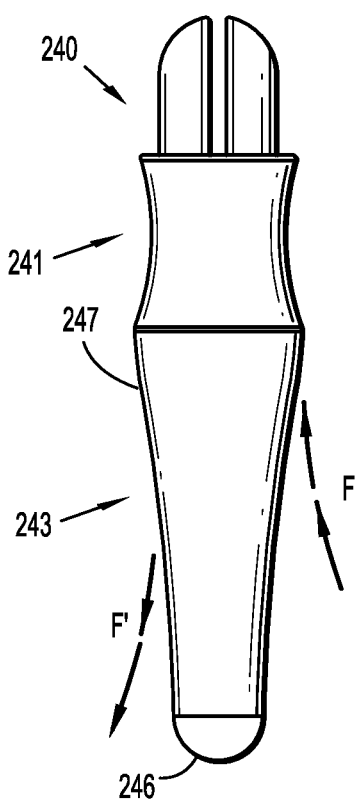
FIG. 5C is a top view of the catheter tip of FIG. 5A.

Referring now to FIGS. 5A-5C, a catheter tip 240 includes a proximal portion 241 and a distal portion 243. The distal portion 243 has a substantially tapered profile that gradually tapers towards a closed distal end 246. The catheter tip 240 defines a pair of side openings 252 disposed along opposed sides of the outer surface 247 of the catheter tip 240. The proximal portion 241 of the catheter tip 240 is a curved spheroid region adjacent the distal portion 243. The curved spheroid region of the proximal portion 241 provides a radially expanding surface proximal to the side openings 252 that directs fluid stream F' away from side openings 252 to minimize recirculation of fluid stream F' in the manner discussed above with respect to catheter tip 140.

Figure 6A:
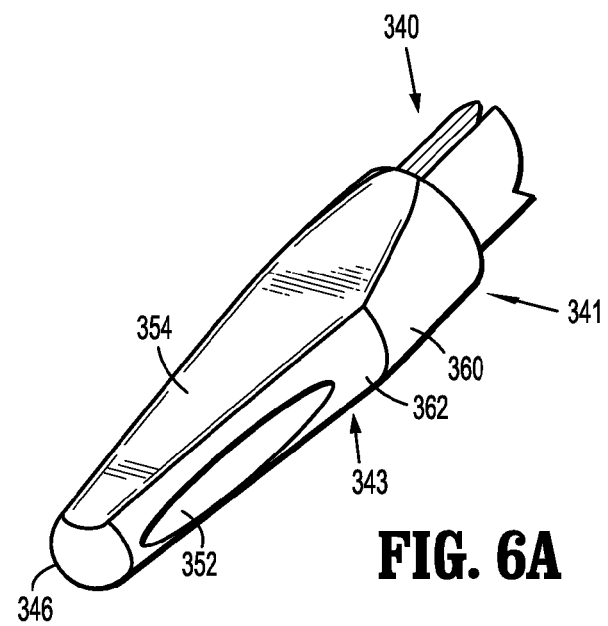
FIG. 6A is a perspective view of an alternate embodiment of a catheter tip having diametrically opposed top and bottom planar surfaces and a proximal portion having top and bottom walls which diverge outwardly as the proximal portion approaches a distal portion of the catheter tip.
Figure 6B:
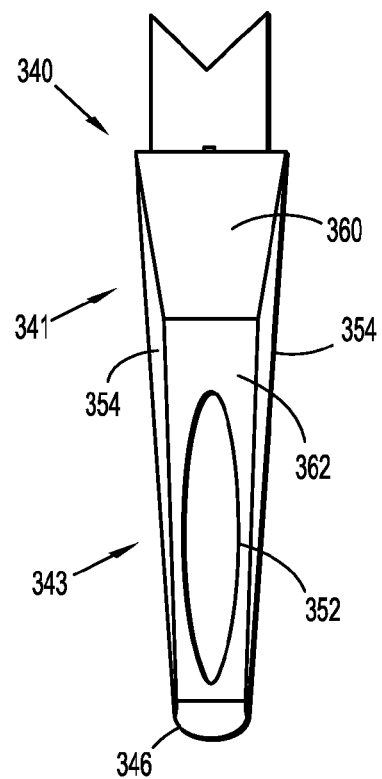
FIG. 6B is a side view of the catheter tip of FIG. 6A.
Figure 6C:
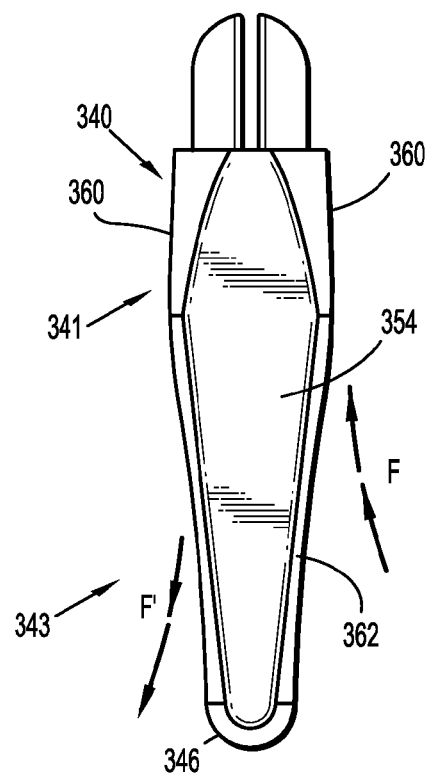
FIG. 6C is a top view of the catheter tip of FIG. 6A.

Referring now to FIGS. 6A-6C, a catheter tip 340 includes diametrically opposed planar surfaces 354, a proximal portion 341 and a distal portion 343. Lateral surfaces 360 of proximal portion 341 diverge outwardly in a direction toward distal portion 343. Each planar surface 354 extends the length of the catheter tip 340 and converges inwardly approaching a blunt distal end 346. Side surfaces 362 of the distal portion 343 taper inwardly in a direction approaching the distal end 346. Side openings 352 are similar to openings 52, 152 and 252 discussed above. Each side opening 352 is positioned along a respective side surface 362. The planar surfaces 354 direct fluid stream F' away from side openings 352 by providing a path of least resistance for fluid stream F' to flow toward distal end 346. The lateral surfaces 360 of the proximal portion 341 also direct fluid outwardly of side openings 352.

Figure 7A:
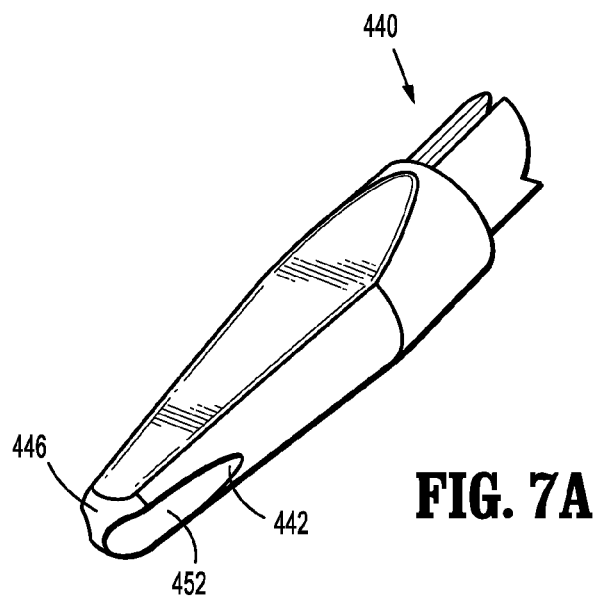
FIG. 7A is a perspective view of a catheter tip including diametrically opposed planar top and bottom surfaces and having side openings extending through the distal end of the catheter tip.
Figure 7B:
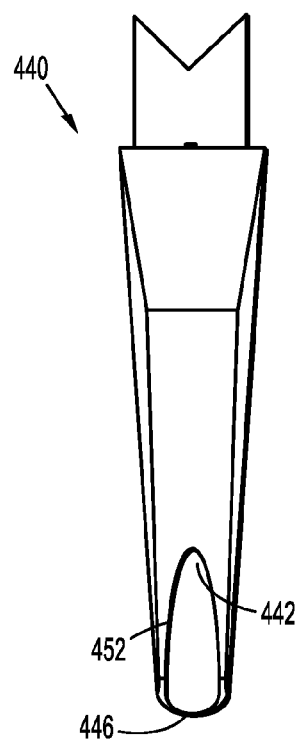
FIG. 7B is a side view of the catheter tip of FIG. 7A.
Figure 7C:
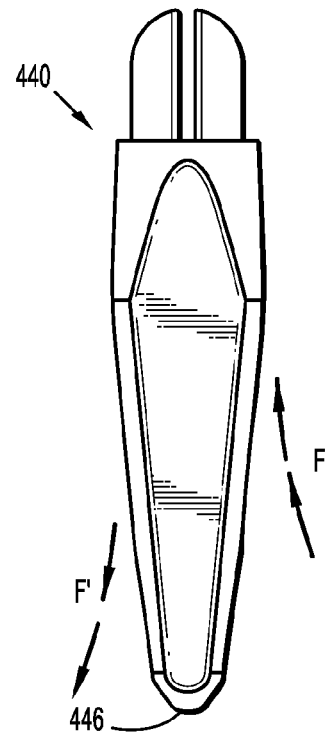
FIG. 7C is a top view of the catheter tip of FIG. 7A.

Referring now to FIGS. 7A-7C, a catheter tip 440 defines a pair of distally positioned, diametrically opposed side openings 452 along the outer surface of a catheter tip 440. The side openings 452 extend through a portion of a distal end 446 of the catheter tip 440. The side openings 452 are in fluid communication with internal lumens 442 of catheter tip 440. The catheter tip 440 functions in a manner similar to that described above with respect to catheter tip 340 (FIGS. 6A-6C).

Referring now to FIGS. 8A-8C, a catheter 510 includes an elongated body 520 and a catheter tip 540 supported at the distal end of the elongated body 520. The elongated body 520 defines first and second lumens (not shown) which extend from a proximal end of the catheter 510 toward the distal end of the catheter 510. In some embodiments, the catheter tip 540 is substantially conical and tapers inwardly in the distal direction to define a blunt or atraumatic end.

The catheter body 520 defines first and second side openings 526 diametrically opposed to one another along the length of body 520. Each side opening 526 is in fluid communication with a respective one of the first and second lumens. Each side opening 526 has an elongated Z-shaped configuration including a rectangular or rhombus-shaped central portion 527a and triangular proximal and distal portions 527b and 527c. The apex of the triangular portion 527b is at the proximal end of the triangular portion 527b and the apex of the triangular portion 527c is at the distal end of the triangular portion 527c. In some embodiments, the rectangular portion 527a defines a transverse axis T (FIG. 8B) which defines an acute angle θ with a longitudinal axis B defined by the catheter body 520. For example, the angle θ can be between about fifteen degrees and about seventy-five degrees. In certain embodiments, sidewalls 529 defining a portion of rectangular portion 527a and triangular portions 527b and 527c are substantially parallel to a longitudinal axis B defined by catheter body 520.

As discussed above, the side openings 526 are symmetrically positioned on opposite sides of the catheter body 520 and each of the side openings 526 communicates with a respective lumen of the catheter 510. The side openings 526 facilitate separation of the fluid flow stream F into the arterial lumen of the catheter 510 and the fluid flow stream F' exiting the venous lumen of the catheter 510. More specifically, because of the configuration of the side openings 526, blood flow has a tendency to flow into a proximal end of the side opening communicating with the arterial lumen of the catheter body 520 and exit the distal end of the side opening 526 communicating with the venous lumen of the catheter body 520. Because of this, the fluid streams F and F' to and from the catheter 510 are spaced to minimize the degree of recirculation within the catheter body 520.

Figure 9C:
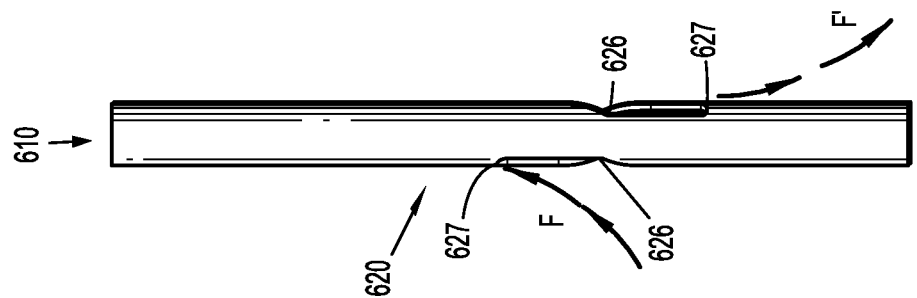
FIG. 9C is a top view of the catheter assembly of FIG. 9A.
Figure 9B:
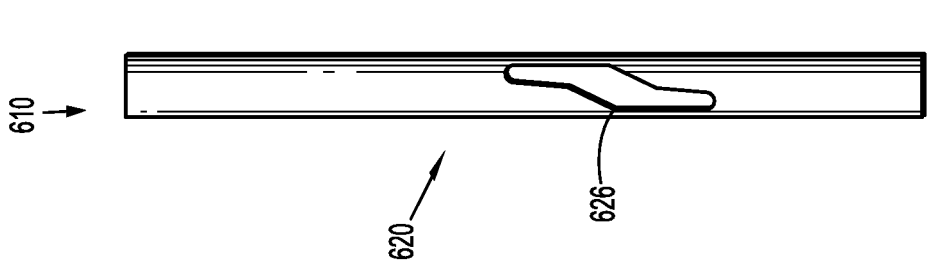
FIG. 9B is a side view of the catheter assembly of FIG. 9A.
Figure 9A:
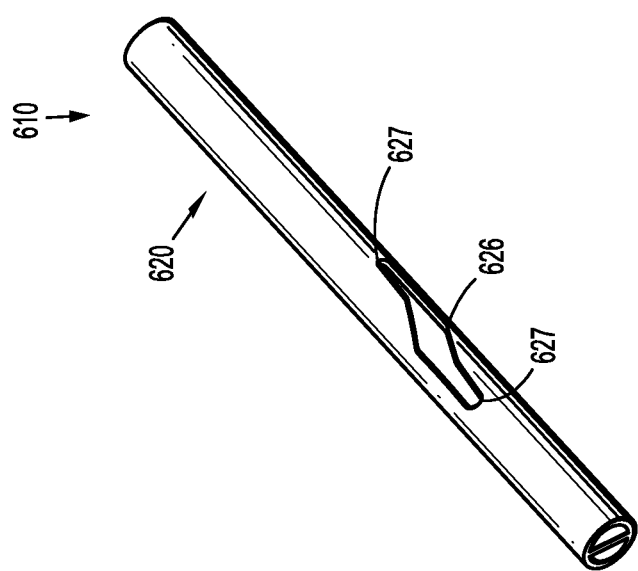
FIG. 9A is a perspective view of a catheter assembly including side openings having rounded ends.

Referring to FIGS. 9A-9C, a catheter 610 includes a body 620 defining side openings 626 that have rounded proximal and distal ends 627. The ingress and egress points for fluid flow streams F, F' through arterial and venous lumens (not shown), respectively, are axially spaced apart as described above. Thus, fluid stream F entering the arterial lumen and fluid stream F' exiting the venous lumen are circumferentially and axially spaced apart, to minimize the degree of recirculation. As compared to sharp edges, the rounded edges 627 of side openings 626 reduce shear stresses on the blood flow to reduce the likelihood of thrombus formation.

Figure 10C:
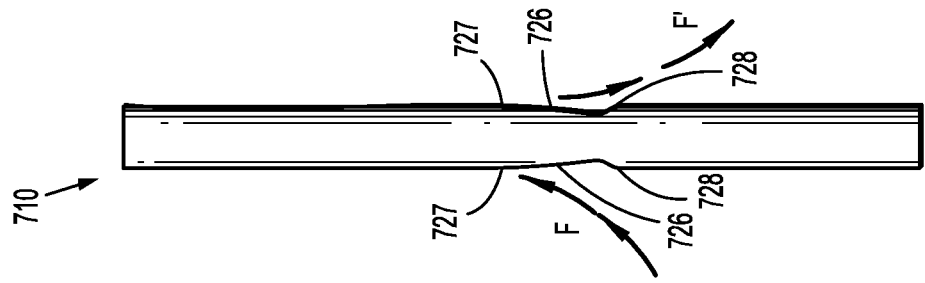
FIG. 10C is a top view of the catheter assembly of FIG. 10A.
Figure 10B:
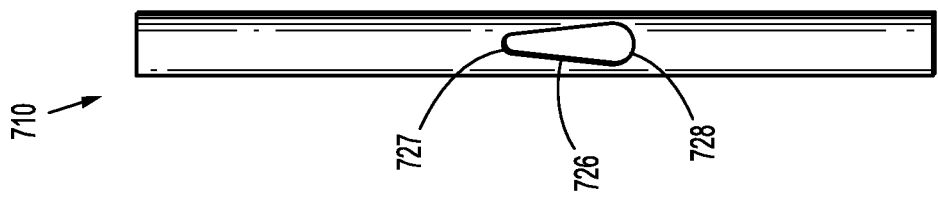
FIG. 10B is a side view of the catheter assembly of FIG. 10A.
Figure 10A:
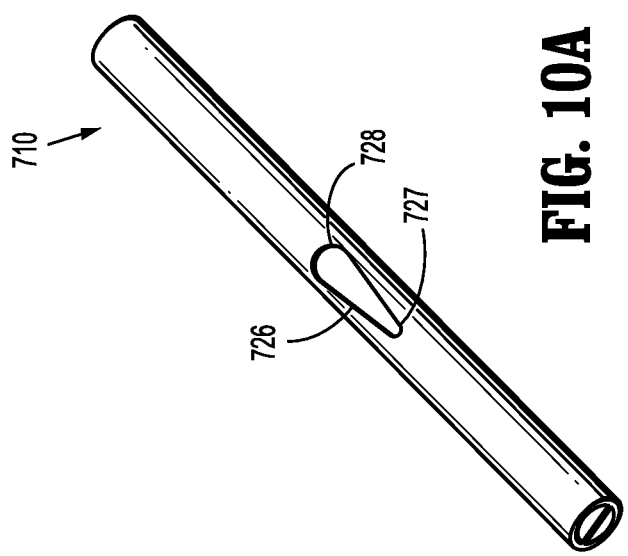
FIG. 10A is a perspective view of a catheter assembly having a catheter body with a pair of diametrically opposed side openings, each shaped as a tapered slot with rounded ends.

Referring to FIGS. 10A-10C, a catheter 710 defines a pair of diametrically opposed side openings 726, each side opening having a proximal end 727 and a distal end 728. The side openings 726 have a substantially teardrop-shaped profile with rounded ends. The taper of the teardrop shape of each side opening 726 tapers proximally from the proximal end 727 to the distal end 728, with the proximal end 727 having a smaller radius of curvature than the distal end 728. Fluid stream F enters an arterial lumen at the proximal end 727. Fluid stream of F' exits a venous lumen at the distal end 728. Accordingly, proximal and distal flow of fluid streams F, F' through respective lumens are both axially and circumferentially spaced to minimize recirculation.

Figure 11C:
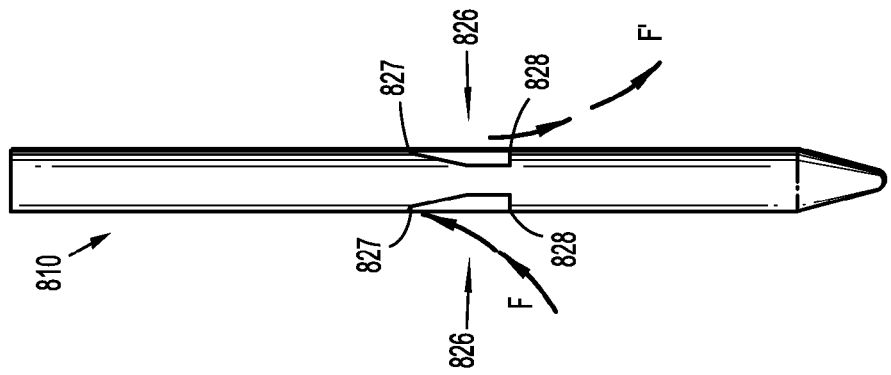
FIG. 11C is a top view of the catheter assembly of FIG. 11A.
Figure 11B:
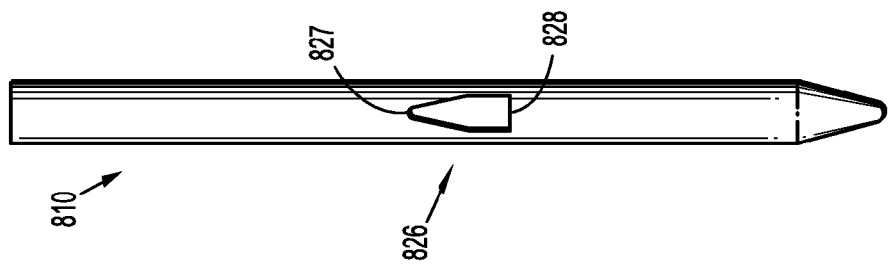
FIG. 11B is a side view of the catheter assembly of FIG. 11A.
Figure 11A:
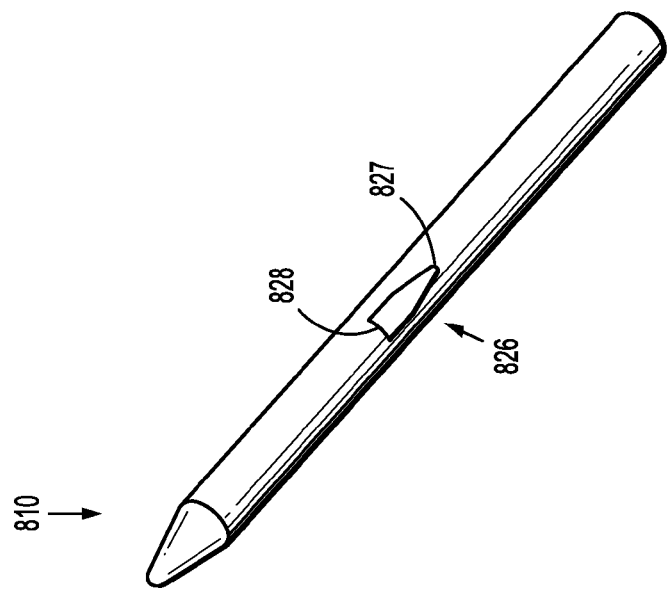
FIG. 11A is a perspective view of a catheter assembly having a catheter body with a pair of diametrically opposed side openings, each having a truncated oval shape with a flat distal wall.

Referring to FIGS. 11A-11C, a catheter 810 defines a pair of diametrically opposed side openings 826. Each side opening 826 has a proximal end 827 and a distal end 828 and an elongated, truncated oval shape. The distal end 828 of each side opening 826 has a generally flat or planar shape. Each side opening 826 tapers proximally and narrows toward the respective proximal end 827, which has a curved shape. Fluid stream F enters an arterial lumen at the proximal end 827 and fluid stream F' exits a venous lumen at the distal end 828. Accordingly, proximal and distal flow of fluid streams F, F' through respective lumens are both axially and circumferentially spaced from one another to minimize recirculation.

Figure 12C:
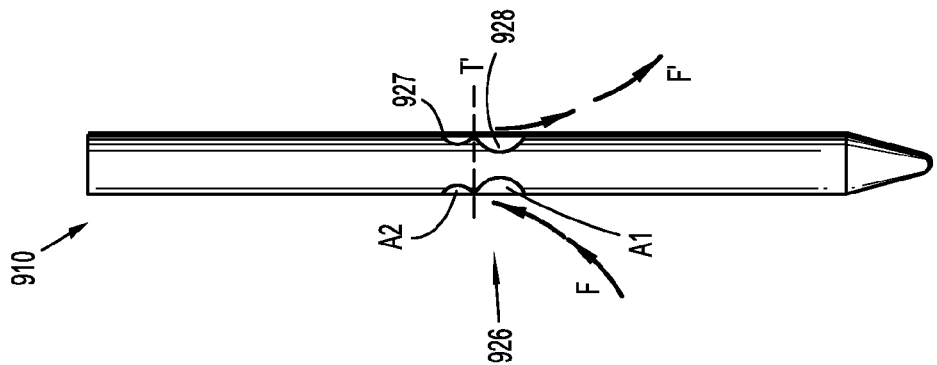
FIG. 12C is a top view of the catheter assembly of FIG. 12A.
Figure 12B:
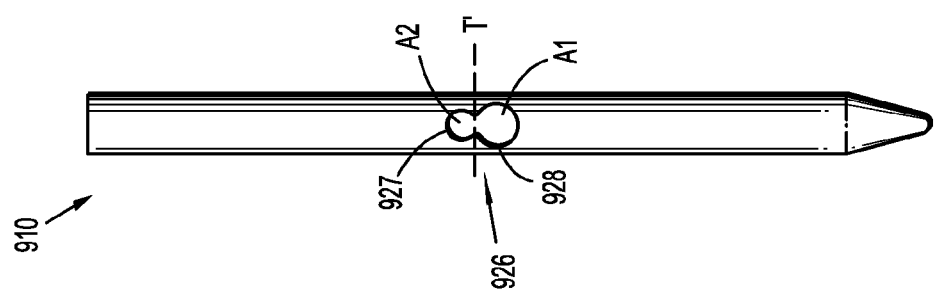
FIG. 12B is a side view of the catheter assembly of FIG. 12A.
Figure 12A:
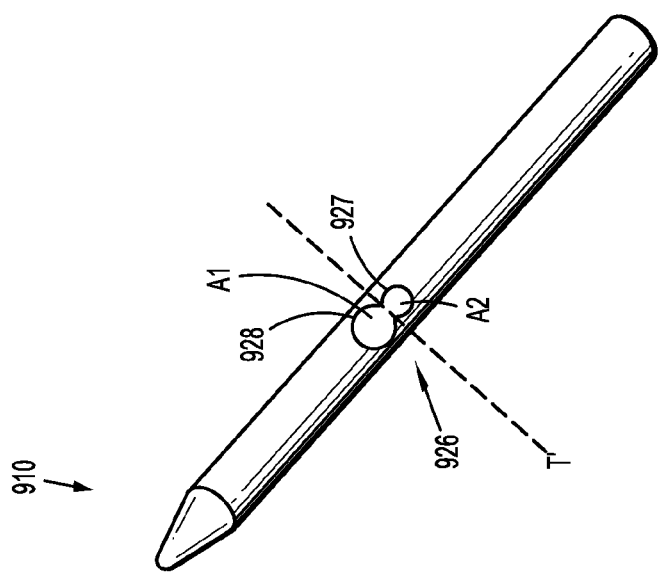
FIG. 12A is a perspective view of a catheter assembly having a catheter body with a pair of diametrically opposed side openings each having a shape defined by a circular distal portion intersecting a smaller circular proximal portion.

Referring to FIGS. 12A-12C, a catheter 910 defines a pair of diametrically opposed side openings 926. Each side opening 926 has a proximal portion 927, a distal portion 928, and a substantially pear-shaped profile. The distal portions 928 of each side opening 926 is arcuate and has a first diameter "A1", and the proximal portion 927 of each side opening 926 is arcuate and has a second diameter "A2" that is smaller than diameter A1. The respective proximal portions 927 and distal portions 928 intersect along a transverse axis T' of catheter 910. Fluid stream F enters an arterial lumen at the proximal portion 927, and fluid stream F' exits a venous lumen at the distal portion 928. Accordingly, proximal and distal flow of fluid streams F, F' through respective lumens are both axially and circumferentially spaced relative to one another to minimize recirculation.

Figure 13C:
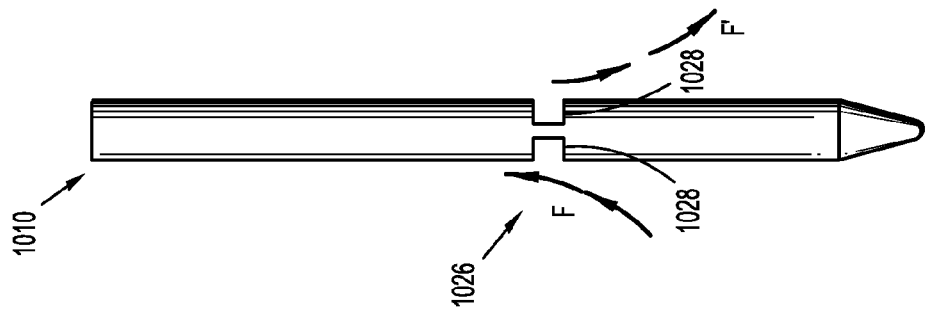
FIG. 13C is a top view of the catheter assembly of FIG. 13A.
Figure 13B:
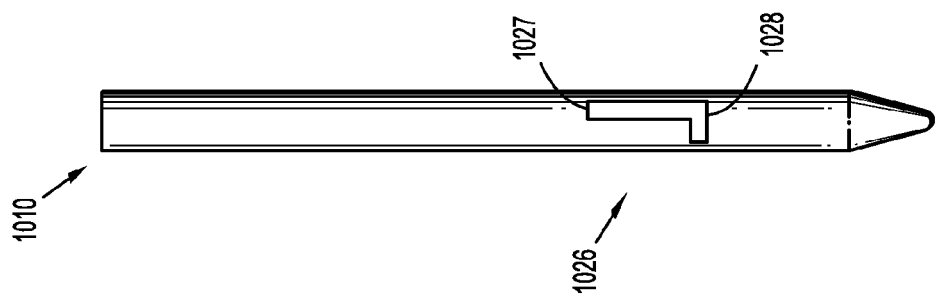
FIG. 13B is a side view of the catheter assembly of FIG. 13A.
Figure 13A:
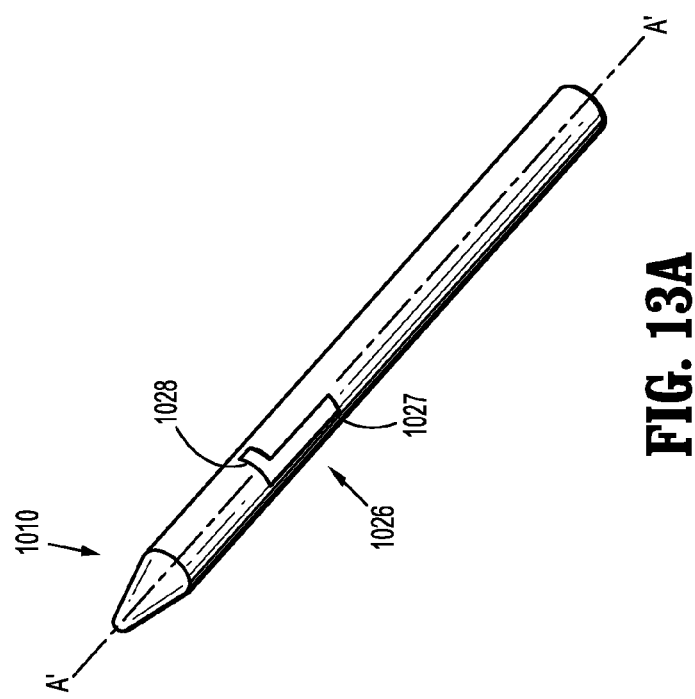
FIG. 13A is a perspective view of a catheter assembly having a catheter body with a pair of diametrically opposed side openings each having an L-shape including rectangular slots intersecting in transverse relation.

Referring to FIGS. 13A-13C, a catheter 1010 defines a pair of diametrically opposed side openings 1026. Each side opening 1026 has a proximal portion 1027 and a distal portion 1028 and has a substantially L-shaped profile. The distal portion 1028 of each side opening 1026 extends across a portion of the surface of the catheter 1010 in transverse relation to a longitudinal axis A' of catheter 1010. The proximal portion 1027 of each side opening 1026 extends along a portion of the surface of the catheter 1010 parallel to the longitudinal axis A' and intersects a respective distal portion 1028. Fluid stream F enters an arterial lumen at the proximal portion 1027 and exits a venous lumen at the distal portion 1028. Accordingly, proximal and distal flow of fluid streams F, F' through respective lumens are both axially and circumferentially spaced from one another.

Figure 14C:
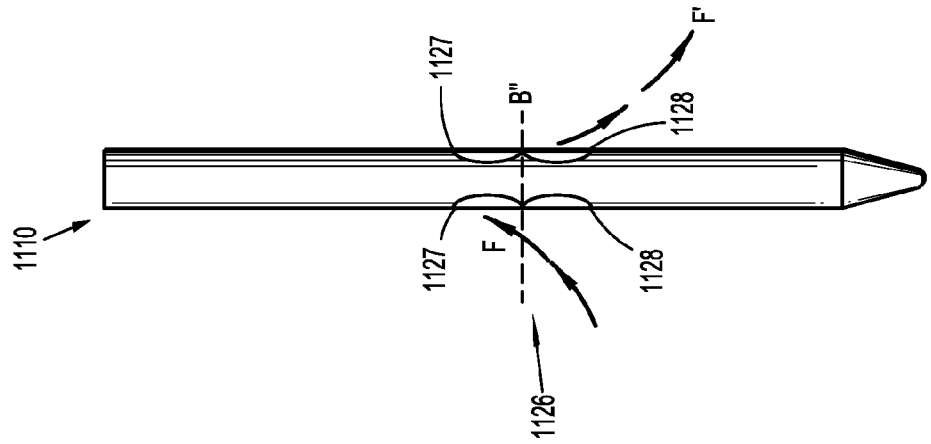
FIG. 14C is a top view of the catheter assembly of FIG. 14A.
Figure 14B:
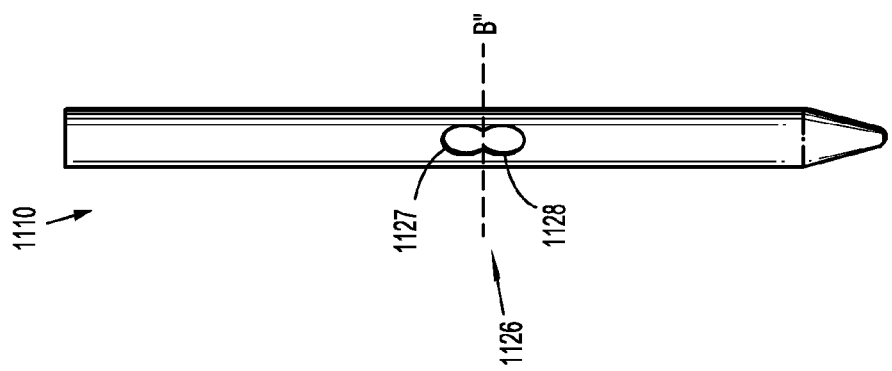
FIG. 14B is a side view of the catheter assembly of FIG. 14A.
Figure 14A:
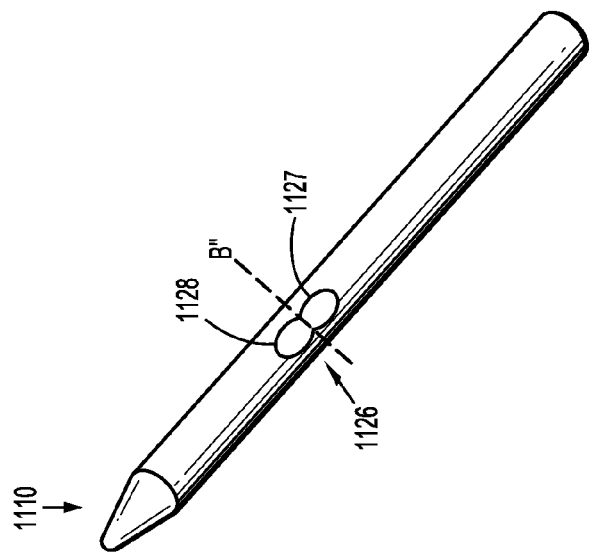
FIG. 14A is a perspective view of a catheter assembly having a catheter body with a pair of diametrically opposed side openings having a shape defined by a circular distal portion intersecting a circular proximal portion.

Referring to FIGS. 14A-14C, a catheter 1110 defines a pair of diametrically opposed side openings 1126. Each side opening 1126 has a proximal portion 1127, a distal portion 1128, and a substantially figure eight-shaped profile. The proximal portion 1127 and distal portion 1128 of each respective side opening 1126 each have a shape defined by an arcuate distal portion intersecting an arcuate proximal portion, and are symmetric about a transverse axis B" of the catheter 1110. Fluid stream F enters an arterial lumen at the proximal portion 1127, and fluid stream F' exits a venous lumen at the distal portion 1128. Accordingly, proximal and distal flow of fluid streams F, F' through respective lumens are both axially and circumferentially spaced from one another to minimize recirculation.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:
1. A medical catheter assembly, comprising:
   an elongate catheter member including a septum defining at least a portion of each of a pair of internal lumens;
   a catheter tip coupled to a distal end of the elongate catheter member and is symmetric about a plane defined by the septum, the catheter tip including a distal portion and a proximal portion, an upper surface, a lower surface, and side surfaces between the upper and lower surfaces, the distal portion including a closed distal end, and the catheter tip defining:
first and second lumens, and
first and second openings in the distal portion of the catheter tip, each opening defined by a respective side surface of the catheter tip, each opening in fluid communication with a respective one of the first and second lumens of the catheter tip and with a respective one of the first and second lumens of the elongate catheter member;
wherein a distance between the upper and lower surfaces of the catheter tip along the proximal portion increases in a distal direction adjacent the distal portion and decreases from a distal end of the proximal portion toward the closed distal end.

2. The medical catheter assembly of claim 1, wherein the proximal portion of the catheter tip is defined by a curved spheroid region.

3. The medical catheter assembly of claim 1, wherein the first and second openings are each an elongate oval.

4. The medical catheter assembly of claim 1, wherein the elongate catheter member defines a longitudinal axis and the first and second side openings are spaced a distance, along the longitudinal axis, from the distal end of the catheter tip.

5. The medical catheter assembly of claim 1, wherein the first and second internal lumens are semicircular in cross-sectional shape.

6. The medical catheter assembly of claim 1, wherein the elongate catheter member and the catheter tip are coupled by at least one connecting member extending therebetween.

7. The medical catheter assembly of claim 6, wherein the at least one connecting member defines a channel in fluid communication with the elongate catheter member and the catheter tip.

8. The medical catheter assembly of claim 7, wherein the at least one connecting member includes a proximal end and a distal end, and the distal end of the connecting member is adjacent one of the first and second side openings.

9. The medical catheter assembly of claim 1, wherein the first and second side openings each have a contoured perimeter.

* * * * *